United States Patent
Santhoff

(10) Patent No.: US 6,919,838 B2
(45) Date of Patent: Jul. 19, 2005

(54) ULTRA-WIDEBAND IMAGING SYSTEM

(75) Inventor: John H. Santhoff, San Diego, CA (US)

(73) Assignee: Pulse-LINK, Inc., Carlsbad, CA (US)

(*) Notice: Subject to any disclaimer, the term of this patent is extended or adjusted under 35 U.S.C. 154(b) by 0 days.

(21) Appl. No.: 10/290,805

(22) Filed: Nov. 8, 2002

(65) Prior Publication Data

US 2003/0090407 A1 May 15, 2003

Related U.S. Application Data

(60) Provisional application No. 60/338,395, filed on Nov. 9, 2001.

(51) Int. Cl.$^7$ .............................................. G01S 13/89
(52) U.S. Cl. ........................................ 342/22; 342/27
(58) Field of Search ........................ 342/22, 27; 367/7

(56) References Cited

U.S. PATENT DOCUMENTS

| | | | |
|---|---|---|---|
| 5,361,070 A | | 11/1994 | McEwan |
| 5,446,461 A | * | 8/1995 | Frazier ........................ 342/22 |
| 5,576,627 A | * | 11/1996 | McEwan ..................... 342/27 |
| 5,668,555 A | | 9/1997 | Starr |
| 5,673,050 A | | 9/1997 | Moussally et al. |
| 5,808,962 A | * | 9/1998 | Steinberg et al. .............. 367/7 |
| 5,900,833 A | | 5/1999 | Sunlin et al. |
| 2002/0175850 A1 | * | 11/2002 | Barnes et al. ................. 342/22 |

OTHER PUBLICATIONS

Withington et al., "Preliminary results of an Ultra–Wideband (Impulse) Scanning Receiver," Military Communications Conference Proceedings, 1999. MILCOM 1999. IEEE, Nov. 1999.*

* cited by examiner

*Primary Examiner*—Ian J. Lobo
(74) *Attorney, Agent, or Firm*—Pulse-LINK, Inc.

(57) ABSTRACT

The present invention comprises a scanner or imager that employs a plurality of ultra-wideband (UWB) transmitters that emit a multiplicity of UWB pulses, which are received by a plurality of receivers. An object or person positioned between the UWB transmitters and receivers can be scanned and subsequently imaged in extreme detail, due to the broad spectral content of the UWB pulses. The UWB scanner can be constructed as a stationary or portable device.

3 Claims, 6 Drawing Sheets

ULTRA-WIDEBAND IMAGING SYSTEM

Priority is claimed to U.S. Provisional Application Ser. No. 60/338,395, filed Nov. 9, 2001, titled "Ultra-Wideband Imaging System," which is referred to and incorporated herein in its entirety by this reference.

FIELD OF THE INVENTION

The present invention generally relates to imaging systems. More particularly the invention concerns an imaging system that employs ultra-wideband technology.

BACKGROUND OF THE INVENTION

A variety of scanning and imaging systems are employed for uses ranging from airport security to biomedical imaging. Some of these systems employ technologies including X-rays, Magnetic Resonance Imaging (MRI), and Nuclear Quadrupole Resonance (NQR). Essentially, there are three types of MRI: Superconductive, Resistive, and Permanent. Superconductive. MRI provides high field strength, but requires constant liquid helium replenishment. Resistive MRI is inexpensive but does not have high field strength. Additionally, it has high operational cost and low field stability. Permanent magnet MRI is the most economical but can weigh in excess of 10 tons and since the magnetic field is supplied by a permanent magnet it cannot be turned off. Additionally, permanent magnet MRIs have low field strength and can only operate in a very controlled temperature range.

Another type of imaging system is zero field nuclear magnetic resonance (NMR), commonly but inaccurately known as NQR. This technology has the advantage over MRI in that it needs no magnetic field to scan an object. NQR scanning technology employs narrow-band radio-frequency (RF) waves that are pulsed to excite the object, or material of interest. The frequency range and pulse duration of the RF waves are selected to identify resonance frequencies of specific material(s) that the system is designed to detect. Thus, NMR scanning technology is most effective when scanning for specific materials.

Therefore, there exists a need for an imaging system that provides a high resolution, gathers a wide array of data relating to any material of interest, and is cost-effective to operate.

SUMMARY OF THE INVENTION

The present invention is directed to a scanning and imaging system, method and apparatus that employs an ultra-wideband (UWB) emitter, or transmitter. One embodiment of the present invention transmits UWB pulses that include "sub-harmonic frequencies" similar to the atomic frequencies of pre-cancerous cell molecules. The cells receive the energy, and then emit energy at a similar frequency. The present invention receives and interprets these emissions and other emissions without employing magnetism.

Another embodiment of the present invention comprises a scanner or imager that employs a plurality of ultra-wideband (UWB) transmitters that emit a multiplicity of UWB pulses, which are received by a plurality of receivers. Due to the broad spectral content of the UWB pulses, an object or person positioned between the UWB transmitters and receivers can be scanned and subsequently imaged in fine detail. The scanner can be constructed as a stationary, or portable device.

These and other features and advantages of the present invention will be appreciated from review of the following detailed description of the invention, along with the accompanying figures in which like reference numerals refer to like parts throughout.

It will be recognized that some or all of the Figures are schematic representations for purposes of illustration and do not necessarily depict the actual relative sizes or locations of the elements shown.

DETAILED DESCRIPTION OF THE INVENTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

The present invention is directed to a scanning and imaging system, method and apparatus that employs at least one ultra-wideband (UWB) emitter, or transmitter. One embodiment of the present invention transmits UWB pulses that include "sub-harmonic frequencies" similar to the atomic frequencies of pre-cancerous cell molecules. The cells receive the energy, and then emit energy at a similar frequency. The present invention receives and interprets these emissions and other emissions without employing magnetism.

Another embodiment of the present invention comprises a scanner or imager that employs a plurality of ultra-wideband (UWB) transmitters that emit a multiplicity of UWB pulses, which are received by a plurality of receivers. Due to the broad spectral content of the UWB pulses, an object or person positioned between the UWB transmitters and receivers can be scanned and subsequently imaged in fine detail. The scanner can be constructed as a stationary, or portable device.

The present invention employs ultra-wideband (UWB), or impulse radio, that uses pulses of electromagnetic energy that are emitted at nanosecond or picosecond intervals (generally tens of picoseconds to a few nanoseconds in duration). For this reason, ultra-wideband is often called "impulse radio." Because the excitation pulse is not a modulated waveform, UWB has also been termed "carrier-free" in that no apparent carrier frequency is evident in the radio frequency (RF) spectrum. That is, the UWB pulses are transmitted without modulation onto a sine wave carrier frequency, in contrast with conventional radio frequency technology. Ultra-wideband generally requires neither an assigned frequency nor a power amplifier, and because UWB employs a "carrier free" architecture, it does not require the use of high frequency carrier generation hardware, carrier modulation hardware, stabilizers, frequency and phase discrimination hardware or other devices employed in conventional frequency domain systems.

Figure 3:
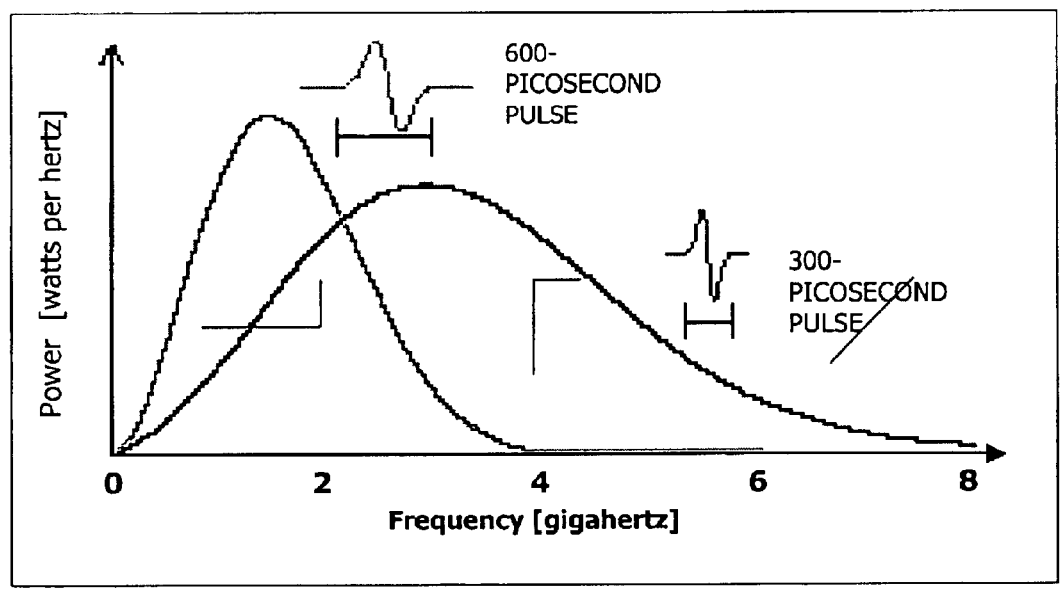
FIG. 3 is an illustration of two ultra-wideband pulses.

Referring to FIG. 3, two UWB pulses are illustrated, a 600 picosecond pulse, and a 300 picosecond pulse. Generally, a 600 picosecond UWB pulse will have about a 1.8 GHz center frequency, with a frequency spread of approximately 4 GHz. A 300 picosecond UWB pulse will have about a 3 GHz center frequency, with a frequency spread of approximately 8 GHz. FIG. 3 illustrates that the narrower the UWB pulse in time, the higher its center frequency and the broader the spread of its frequency spectrum. This is because frequency is inversely proportional to the time duration of the pulse. Thus, UWB pulses generally do not operate within a specific frequency.

Further details of UWB technology are disclosed in U.S. Pat. No. 3,728,632 (in the name of Gerald F. Ross, and titled: Transmission and Reception System for Generating and Receiving Base-Band Duration Pulse Signals without Distortion for Short Base-Band Pulse Communication System), which is referred to and incorporated herein in its entirety by this reference.

Also, because the UWB pulse is spread across an extremely wide frequency range, the power sampled at a single, or specific frequency is very low. For example, an UWB one-watt signal of one nano-second duration spreads the one-watt over the entire frequency occupied by the pulse. Thus, at any single frequency, the UWB pulse power present is one nano-watt (for a frequency band of 1 GHz). Generally, a multiplicity of UWB pulses are transmitted at relatively low power (when sampled at a single, or specific frequency), for example, at less than −30 power decibels to −60 power decibels, which minimizes interference with conventional radio frequencies. The multiplicity of UWB pulses of the present invention may be transmitted in a range between about −40 dBm/Hz to about −140 dBm/Hz.

One embodiment of the present invention can be employed to scan and image humans and animals to identify medical conditions, such as cancer, or to perform preventative biological scanning. For example, the biochemical reactions that occur when a pre-cancerous cell undergoes attack are numerous. The cell breaks down in an uneven manner and forms its own vascular system, causing among other things increased blood flow to the cells. The body attempts to fight the breakdown by producing an enzyme called Hematoporphyrin, which attaches to the pre-cancerous cells. The enzyme is unsuccessful in repairing the cell, and the cell eventually completely breaks down, penetrating the membrane walls of nearby organs. The cancer now multiplies. These pre-cancerous cells can be identified in a number of ways. First, by their increased blood flow to and from the cells (vasculation); second, by the distinct way the cells break down into uneven pairs; third, by the enzyme that attaches and attempts to repair; and fourth by the chemical composition of the cancer itself The molecular structures of these cells have unique chemical properties. By using spectroscopy (the study of chemical tissues), it may be possible to define and identify them. In MRI and more accurately magnetic resonance spectroscopy (MRS), magnetism and pulses of radio-frequency (RF) are used to excite atoms. When the RF pulse is applied to an atom, it "tips." That is when the RF is discontinued, the atom returns to a normal state, giving off RF of the same frequency as was applied.

One embodiment of the present invention may emit a plurality of UWB pulses that, because of their broad frequency content, can "tip" a number of different atoms. These "tipped" atoms can then be identified, and used to diagnose, or treat any number of different medical conditions. This embodiment of the present invention can also be employed to detect the emission of radiation from a material, substance, or object when it returns to its normal configuration from an excited state due to the energy received from the radiated UWB pulse. Another embodiment of the present invention can be applied to improve existing scanning techniques such as CT, PET, Ultrasound, and NMR.

Figure 1A:
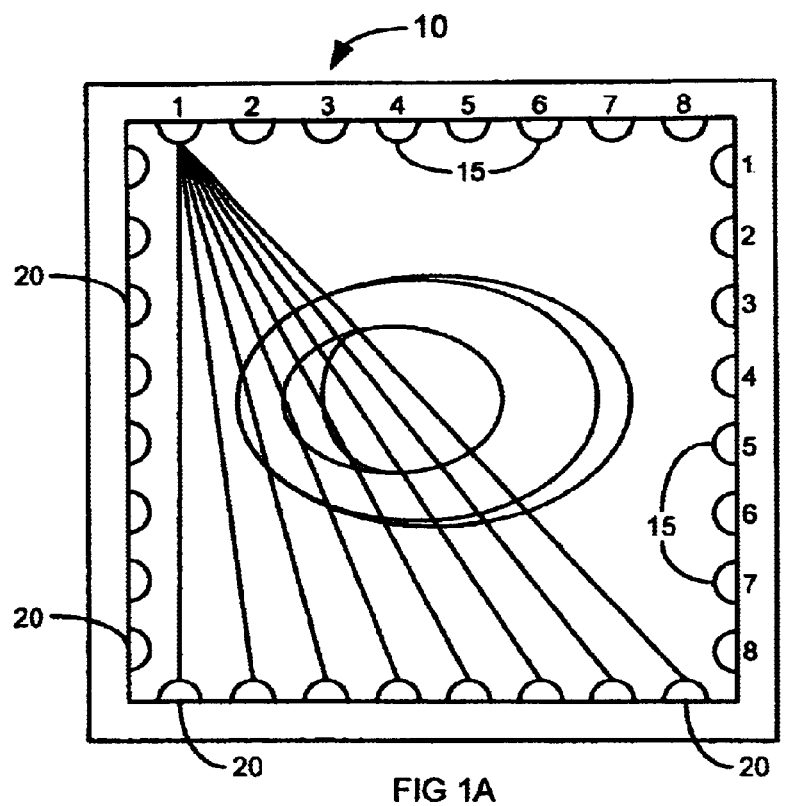
FIGS. 1A–1H are front elevation views of one embodiment of the present invention scanner showing UWB emitters emitting UWB pulses.
Figure 1B:
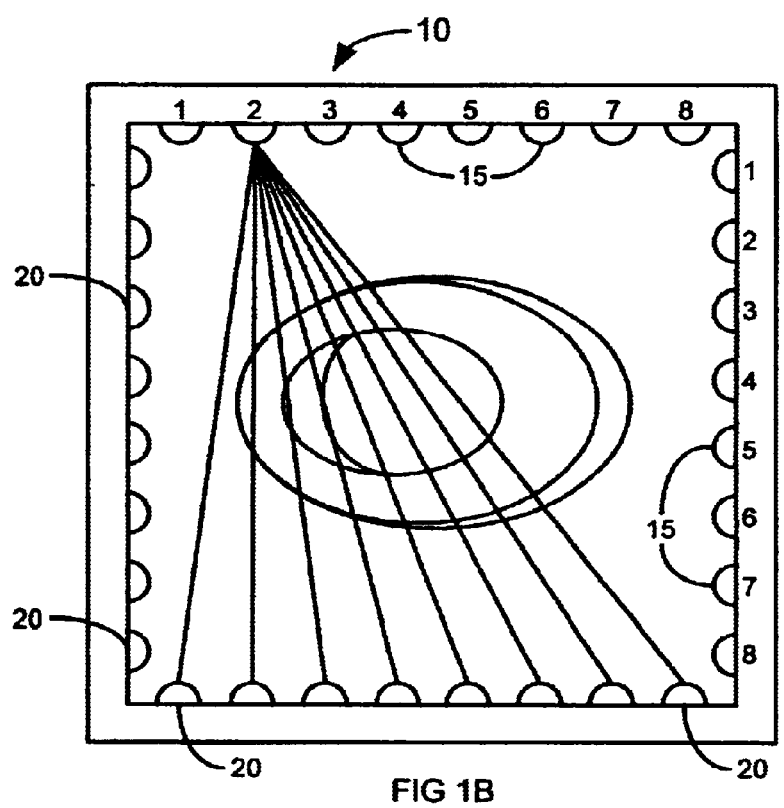
Figure 1C:
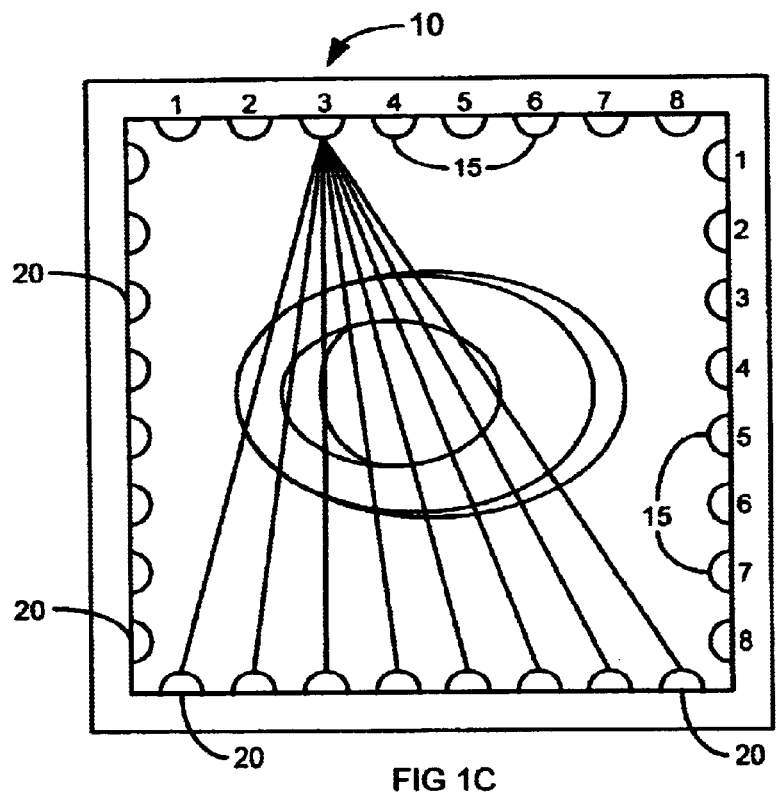
Figure 1D:
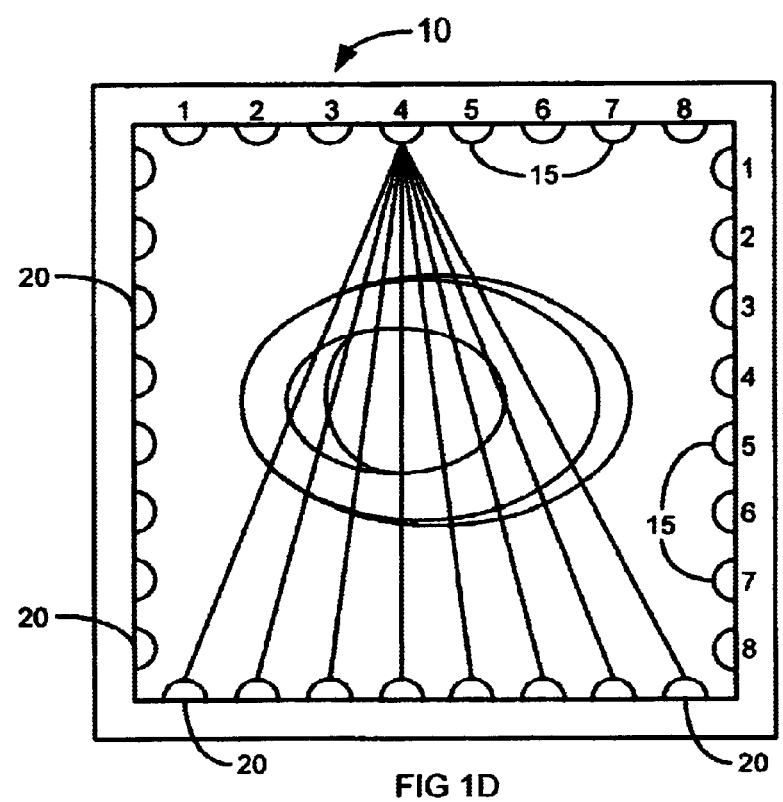
Figure 1E:
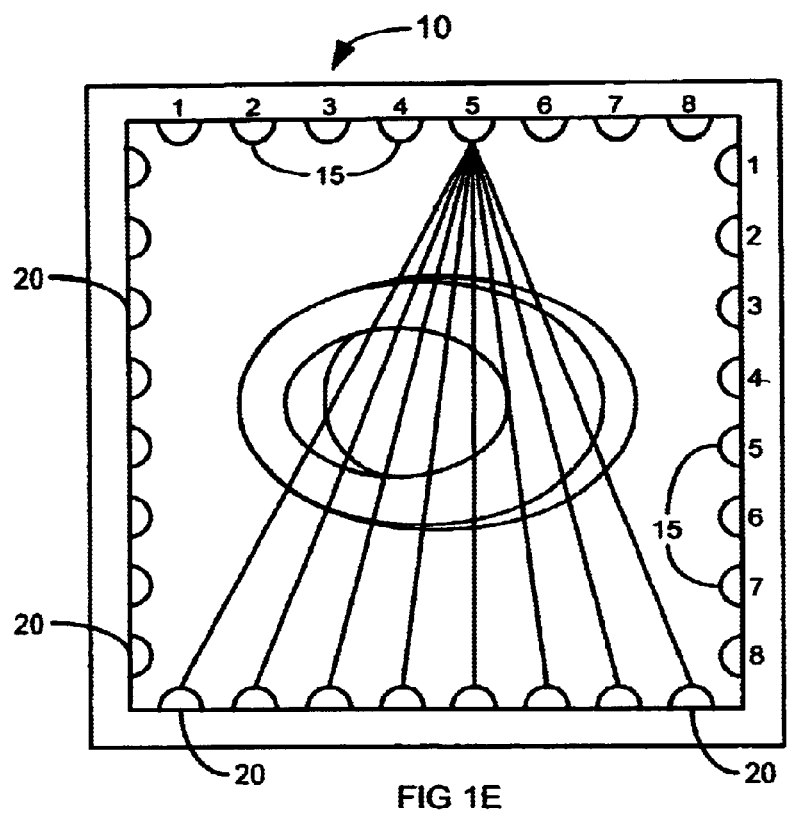
Figure 1F:
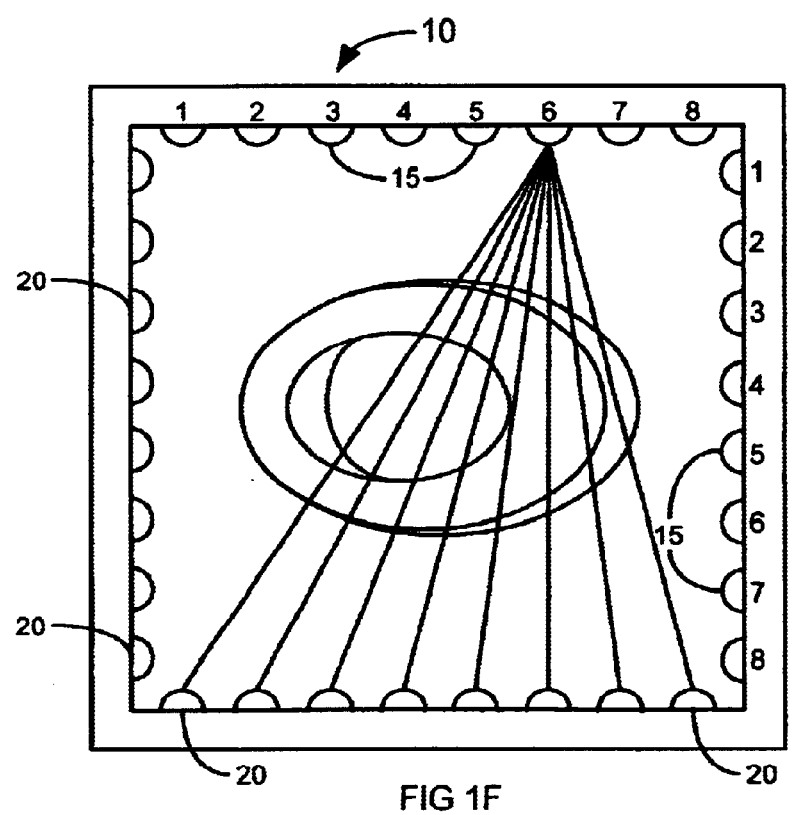
Figure 1G:
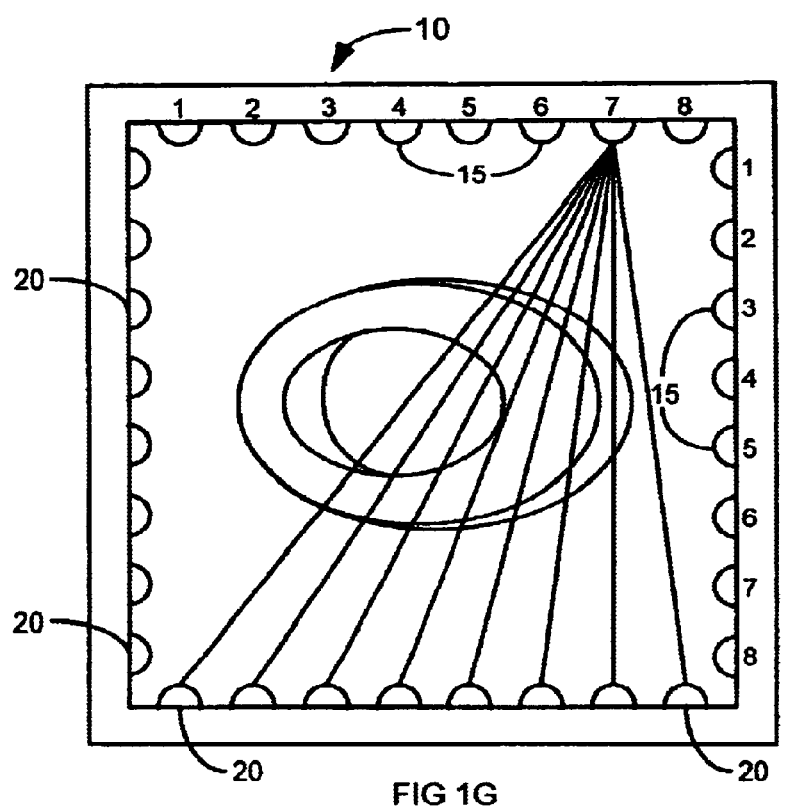
Figure 1H:
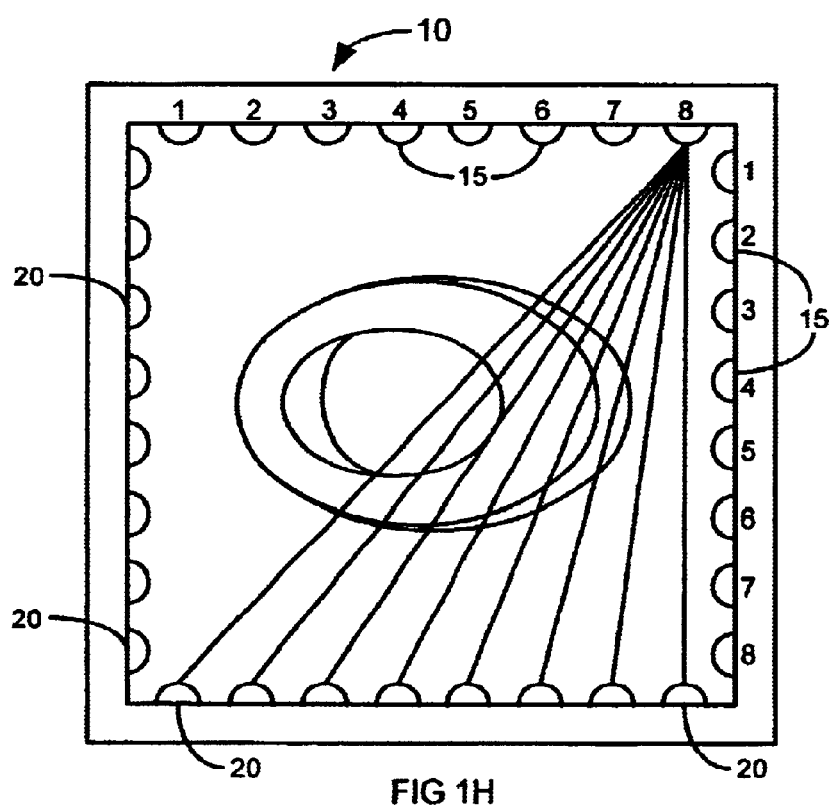

Referring now to FIGS. 1A–1H, an ultra-wideband scanner/imager 10 is illustrated. Arranged along the top, and/or bottom, and/or sides of the ultra-wideband scanner/imager 10 are a plurality of UWB emitters 15. Opposite the emitters are a plurality of UWB receiving antennas 20. Illustrated in FIGS. 1A are eight emitters 15 positioned along the top of the ultra-wideband scanner/imager 10, and eight receiving antennas 20 arranged along the bottom of the ultra-wideband scanner/imager 10. The ultra-wideband scanner/imager 10 may have emitters 15 and receiving antennas 20 arranged on the sides as well. Alternate embodiments may have as many as 1000 emitters 15 and receivers 20.

The emitters 15 can be fired off sequentially, one through eight, as illustrated in FIGS. 1A through 1H. Alternatively, the emitters 15 can be fired off in a non-sequential pattern. Since the UWB pulse is transmitted omni-directionally, all the receiving antennas 20 receive the UWB pulse emitted by each emitter 15. In a preferred embodiment of the present invention, the distance form one emitter 15 to the receiving antenna 20 is about 10 feet. Therefore, at the speed of about one foot per nano-second, the UWB pulse takes about ten nano-seconds to reach the receiving antennas 20. In this embodiment, to eliminate any multi-path problems, the ultra-wideband scanner/imager 10 will wait 20 nano-seconds before moving on in its scanning sequence. In the case of one thousand emitters 15 and one thousand receivers 20 there are one million samples collected in approximately 30 milli-seconds. On feature of the present invention is that an object can be scanned in an extremely short time, thereby enabling a very large number of objects to be scanned. For example, the present invention may be employed in a manufacturing environment, to scan mass-produced objects.

Figure 2:
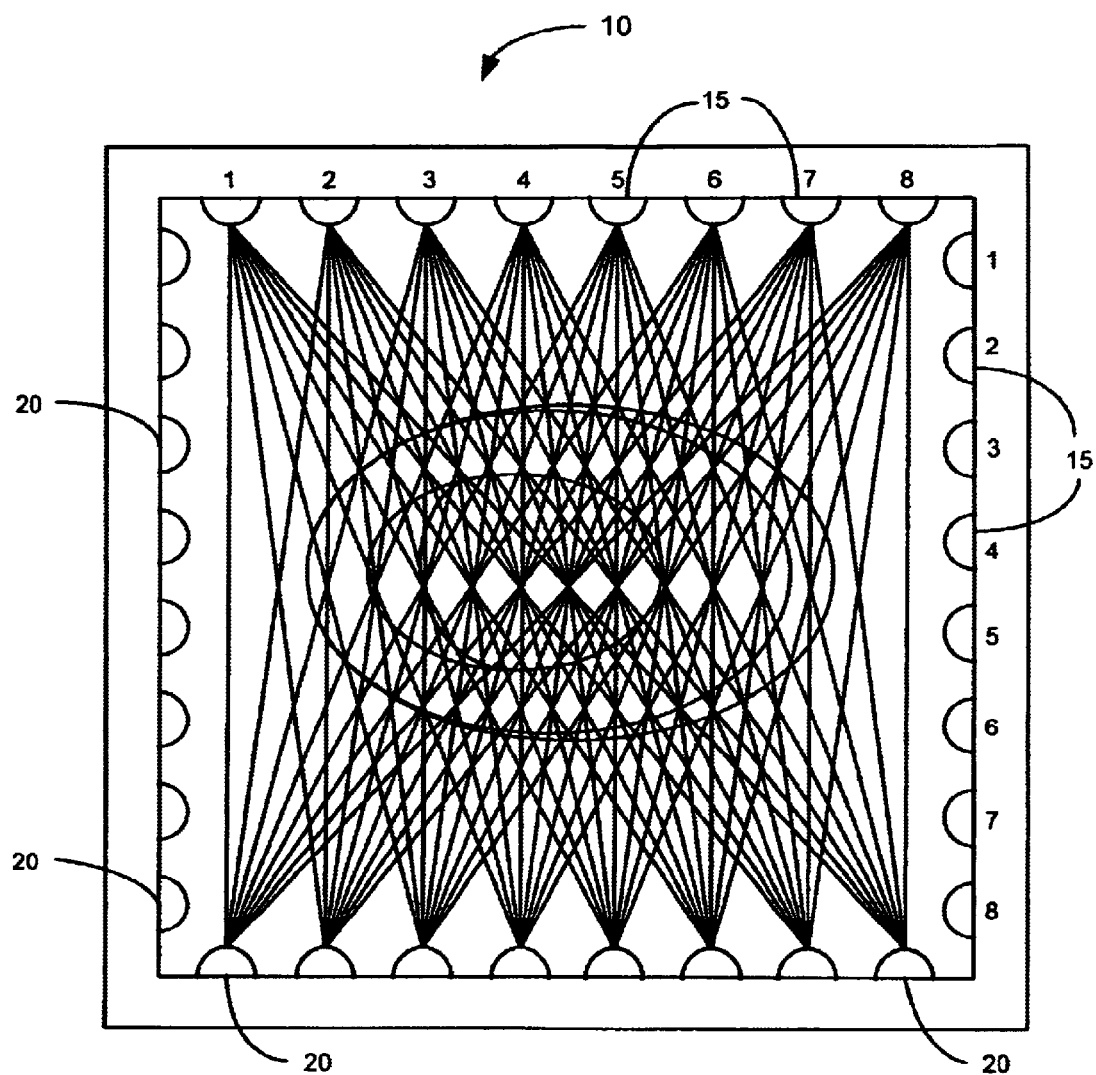
FIG. 2 is front elevation view of another embodiment of the present invention scanner showing UWB emitters emitting UWB pulses from the top and bottom of the scanner.

If necessary, the scanning process can be repeated using the emitters 15 and receiving antennas 20 located on the X-axis, or vertical surfaces of the ultra-wideband scanner/imager 10, as shown in FIG. 2. In addition, emitters 15 and receivers 20 can be located on the Z-axis.

The samples obtained from a scan can be used to form images of the person, or object that has passed through the ultra-wideband scanner/imager 10. Sequential images can be formed from the "slices" of the object, or the entire object can be rendered in a 3-D visualization. One method of 3-D visualization of the present invention uses a propagation time to estimate a density of the scanned material. The denser an object, the longer it takes for a UWB pulse to traverse the object. Once the density of an object, or material is known, many other material characteristics can be determined.

Another embodiment of the present invention can be used for non-destructive testing. For example, a natural gas pipe can be inspected to determine the integrity of welds, and the integrity of the pipe. An embodiment of the present invention constructed for pipe inspection may comprise two separate, portable ultra-wideband scanner/imager 10. The emitting component would be placed inside the pipe, with the receiving component placed on the outside of the pipe, or vice-versa. The ultra-wideband scanner/imager 10 would then traverse the pipe, scanning areas of interest. Other examples of non-destructive testing include testing concrete structures to determine their integrity after an earthquake, or oil pipes can be scanned to evaluate weld integrity, or to reveal manufacturing defects In contrast to MRI, NMR, and NQR, the ultra-wideband (UWB) technology employed by the present invention transmits a time domain pulse. In doing so the pulse energy is spread across an extremely wide frequency band. UWB needs no external magnetic field, thus saving manufacturing cost. This a substantial advantage over MRI systems, as the magnets are the most costly components of an MRI system.

In addition, in the typical NQR system, a very narrow frequency band response is desired, since it is screening for a specific compound or set of compounds. The very broad frequency spectrum generated by the UWB emitters 15 of the present invention allows the ultra-wideband scanner/imager 10 to obtain much more data about the object scanned.

In contrast to imaging radar, the present invention does not employ radar techniques. Radar requires the detection of the reflected radiation from the object. The complex reflectivity function of the material imparts both a phase and amplitude deviation to the return. The receiving antenna collects the radar returns. An image is then formed from this phase history data. The present invention obtains imaging information from the UWB pulses that pass through the scanned object.

One embodiment of the present invention, the UWB pulse penetrates the material and is received after passing through the material. Additionally, since the object being imaged is within the ultra-wideband scanner/imager 10, higher resolutions are possible at lower power. Due to the short duration of a UWB pulse it occupies a wide frequency spectrum. This is desirable since a broad spectral content pulse can gather data at a wider frequency range than a more limited frequency band. RF exposure in the present invention is minimal since the amount of energy required for a UWB scan is significantly less than conventional imaging or scanning methods.

In a preferred embodiment of the present invention, the received signal is collected and digitized at each receiver 20. The signal is then stored in a memory, processed into a visualization such as an image, and can be stored in a data storage recorder for later analysis. Since the relative positions of the emitters 15 and receivers 20 are fixed, time durations from transmission to reception can assist in the determination of material density. In addition, image processing and data visualization techniques can be employed to cognitively enhance the imagery obtained from the ultra-wideband scanner/imager 10.

The ultra-wideband scanner/imager 10 may include several components, including a controller, a waveform generator, static and dynamic memory, data storage devices, a receiver, an interface, one or more devices for data access management, and associated cabling and electronics. One or more of the above-listed components may be co-located or they may be separate devices, and the ultra-wideband scanner/imager 10 may include some, or all of these components, other necessary components, or their equivalents. The controller may include error control, and data compression functions. Alternative embodiments of the ultra-wideband scanner/imager 10 may employ hard-wired circuitry used in place of, or in combination with software instructions. Thus, embodiments of the ultra-wideband scanner/imager 10 are not limited to any specific combination of hardware or software.

Thus, it is seen that ultra-wideband scanning and imaging system is provided. One skilled in the art will appreciate that the present invention can be practiced by other than the above-described embodiments, which are presented in this description for purposes of illustration and not of limitation. The description and examples set forth in this specification and associated drawings only set forth preferred embodiment(s) of the present invention. The specification and drawings are not intended to limit the exclusionary scope of this patent document. Many designs other than the above-described embodiments will fall within the literal and/or legal scope of the following claims, and the present invention is limited only by the claims that follow. It is noted that various equivalents for the particular embodiments discussed in this description may practice the invention as well.

What is claimed is:

1. A method of scanning an object, the method comprising the steps of:

providing at least two ultra-wideband pulse emitters, and a receiver;

substantially eliminating an ultra-wideband pulse multi-path interference by sequentially emitting at least two ultra-wideband pulses toward the object;

receiving the ultra-wideband pulses;

determining a time differential between a portion of the ultra-wideband pulses that did not pass through the object, and a portion of the ultra-wideband pulses that passed through the object;

determining a density of the object based on the a time differential between the portion of the ultra-wideband pulses that did not pass through the object, and the portion of the ultra-wideband pulses that passed through the object; and determining a material characteristic of the object based on the density of the object;

wherein the material characteristic is selected from a group consisting of: a material density, a material composition, a material type and a material shape.

2. A method of scanning an object, the method comprising the steps of:

providing an ultra-wideband pulse emitter, and a receiver;

emitting an ultra-wideband pulse toward the object, with at least a portion of the ultra-wideband pulse passing through the object;

receiving the ultra-wideband pulse, including the portion of the ultra-wideband pulse that passed through the object;

determining a time differential between a portion of the ultra-wideband pulse that did not pass through the object, and a portion of the ultra-wideband pulse that passed through the object;

determining a density of the object based on the a time differential between a portion of the ultra-wideband pulse that did not pass through the object, and the portion of the ultra-wideband pulse that passed through the object; and determining a material characteristic of the object based on the density of the object;

wherein the material characteristic is selected from a group consisting of: a material density, a material composition, a material type and a material shape.

3. A system for scanning an object, comprising:

an ultra-wideband pulse emitter, and a receiver;

logic for emitting an ultra-wideband pulse toward an object, with at least a portion of the ultra-wideband pulse passing through the object;

logic for receiving the ultra-wideband pulse, including the portion of the ultra-wideband pulse that passed through the object; and logic for determining a time differential between a portion of the ultra-wideband pulse that did not pass through the object, and the portion of the ultra-wideband pulse that passed through the object.

* * * * *